United States Patent [19]

Sundermann

[11] 4,042,567

[45] Aug. 16, 1977

[54] S-TRIAZINE PREPOLYMERS AND A PROCESS FOR THEIR PRODUCTION

[75] Inventor: Rudolf Sundermann, Leverkusen, Germany

[73] Assignee: Bayer Aktiengesellschaft, Germany

[21] Appl. No.: 635,589

[22] Filed: Nov. 28, 1975

[30] Foreign Application Priority Data

Dec. 4, 1974 Germany .............................. 2457154

[51] Int. Cl.² ............................................ C08G 65/40
[52] U.S. Cl. ................................... 260/49; 260/47 R; 260/61
[58] Field of Search .................. 260/49, 47 R, 47 CP, 260/47 CZ, 61

[56] References Cited

U.S. PATENT DOCUMENTS

| 2,481,156 | 9/1949 | Schaefer | 260/2 |
| 3,108,029 | 10/1963 | Wohnsiedler et al. | 156/330 |
| 3,654,192 | 4/1972 | Vogel | 260/2 R |
| 3,960,783 | 6/1976 | Seltzer et al. | 260/2 R |

Primary Examiner—Lester L. Lee
Attorney, Agent, or Firm—Connolly and Hutz

[57] ABSTRACT s-Triazine prepolymers with aromatic cyanate groups are obtained by condensation of aromatic di- or polyhydroxy compounds with 0.01 to 0.5 mol of 4,6-dichloro-s-triazine per one hydroxy group. Subsequently the condensation products are reacted with cyanogen halide in the presence of a base. s-Triazine prepolymers may be polymerized to form hard plastics with resistance to high temperature.

5 Claims, No Drawings

S-TRIAZINE PREPOLYMERS AND A PROCESS FOR THEIR PRODUCTION

It is known that difunctional or polyfunctional cyanic acid esters can be polymerised to form high molecular weight polytriazines (German Auslegeschrift No. 1,190,184). The polymerisation reaction, which is highly exothermic, passes through a so-called "B-stage" and is accompanied by relatively heavy shrinkage (Kunststoffe, Vol. 58, page 829 (1968). This gives rise to various disadvantages, especially to regard to processing, for example, to form glass-fibre reinforced mouldings and also in regard, for example, to the dimensional stability of the mouldings produced. In order to avoid the disadvantages of direct polymerisation, it has already been proposed to produce prepolymers by interrupting the polymerisation reaction by cooling after about 30 to 65% of the cyanic acid ester groups have reacted (U.K. patent specification No. 1,305,762).

It has now been found that s-triazine prepolymers can be produced with advantage by condensing aromatic dihydroxy of polyhydroxy compounds with 0.01, preferably with 0.1 and more especially with 0.2 to less than ½ mol of 4,6-dichloro-s-triazines per hydroxyl group, and subsequently reacting the free hydroxyl groups of the resulting condensate with halogen cyanide in the presence of a base.

The 4,6-dichloro-s-triazines used as starting compounds in the process according to the invention are known from A. Weissberger "The chemistry of Heterocyclic Compounds" (s-Triazines and Derivatives), Vol. 13, pages 67–99 and 147–184, Interscience Publishers Inc., New York, 1959, and correspond to compounds of general formula (I) below

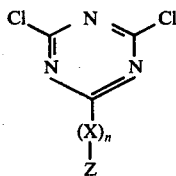
(I)

in which $n$ represents the number 0 or 1 and X and 2 have the same meaning as indicated in formulae II and III. If $n$ represents the number 1 compounds of the formula II result

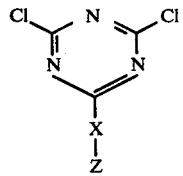
(II)

in which

X represents oxygen (—o—), sulphur (—s—) or nitrogen (— NH — or —NZ'—) and

Z,Z' represent an alkyl, cycloalkyl or aryl radical.

Suitable alkyl radicals are straight-chain and branched chain saturated alkyl radicals with 1 to 36 carbon atoms, preferably with 1 to 20 carbon atoms and more especially with 1 to 18 carbon atoms, straight-chain and branched unsaturated alkyl radicals with 2 to 36 carbon atoms, preferably with 2 to 20 carbon atoms and more especially with 2 to 18 carbon atoms, which may optionally be substituted by halogen (fluorine, chlorine, bromine, iodine), alkoxy groups or dialkyl amino groups with 1 to 9 carbon atoms in each case; for example methyl, ethyl, propyl, isopropyl, n-butyl, isobutyl, tert-butyl, the isomeric pentyl, hexyl and octyl radicals, also nonyl, decyl, dodecyl, tetradecyl, hexadecyl and octadecyl radicals. In addition, 2-chloroethyl, 1-chloroisopropyl, 2,3-dibromopropyl, 1,3-dichloroisopropyl, 2,2,2-trichloroethyl, propenyl, 2-methyl-3-isobutenyl 9-octadecenyl, 2-propinyl, 3-butinyl-2,2-methoxy ethyl, 2-ethoxy ethyl, 2-propoxy ethyl, 2-isopropoxy ethyl, 2-butoxy ethyl, 2-($\beta$-methoxyethoxy)-ethyl, 2-($\beta$-ethoxyethoxy)-ethyl, 2-methoxy butyl, 1,3-diethoxy isopropyl, 2-cyanoethyl, 2-dimethyl aminoethyl, 2-diethyl aminoethyl, 2-dibutyl aminoethyl, 2-($\beta$-dimethylaminoethoxy)-ethyl, 3-dimethyl aminopropyl, 2-dimethyl aminoisopropyl, 2-diethyl aminoisopropyl and 1,3,bis-dimethyl aminoisopropyl.

Suitable cycloalkyl radicals are cycloalkyl radicals with 5 to 14 carbon atoms, which may optionally be substituted by alkyl groups with 1 to 9 carbon atoms, more especially cyclopentyl, cyclohexyl, the methyl cyclohexyls, cyclohexyl methyl, tert-butyl cyclohexyl and decahydronaphthyl.

Suitable aryl radicals are phenyl, naphthyl, which may optionally be substituted by one or more of the following groups, alkyl groups with 1 to 9 carbon atoms, phenyl or napthyl, alkoxy groups with 1 to 9 carbon atoms in the alkyl chain, phenyloxy or naphthyloxy, nitro, halogen (fluorine, chlorine, bromine, iodine), acyl with 2 to 6 carbon atoms, alkyl mercapto with 1 to 9 carbon atoms, phenyl or naphthyl mercapto, cyano, carboxylic acid phenyl or naphthyl esters, carboxylic acid alkyl esters with 1 to 18 carbon atoms in the alcohol component, carboxylic acid dialkyl amide with 1 to 9 carbon atoms in the alkyl group, carboxylic acid diphenyl or napthyl amide, dialkyl amino with 1 to 18 carbon atoms in the alkyl chain, diphenyl or napthyl amino, alkyl sulphonyl with 1 to 9 carbon atoms, phenyl or naphthyl sulphonyl, sulphonic acid phenyl or naphthyl ester, sulphonic acid dialkyl amide with 1 to 9 carbon atoms, sulphonic acid diphenyl or naphthyl amide.

The following groups are mentioned by way of example for the purposes of illustration: phenyl,o-methyl phenyl, m-methyl phenyl, p-methyl phenyl, 2,4-dimethyl phenyl, 3,5-dimethyl phenyl, 2,6-dimethyl phenyl, o-ethyl phenyl, m-ethyl phenyl, p-ethyl phenyl, 2,4-diethyl phenyl, 2-n-propyl phenyl, m-isopropyl, 2-methyl-4-isopropyl phenyl, 4-ethyl-2-isopropyl phenyl, 2,4-diisopropyl phenyl, 4-butyl phenyl, 2-tert-butyl phenyl, 4-tert-butyl phenyl, 2,4-di-tert-butyl phenyl, 2,6-di-tert-butyl phenyl, 2-methyl 4-tert-butyl phenyl, the isomeric pentyl phenyls, the isomeric hexyl phenyls, octyl phenyls, p-nonyl phenyl, the isomeric diphenylyls, p-cumyl phenyl, o-methoxy phenyl, p-methoxy phenyl, p-ethoxy phenyl, o-phenoxy phenyl, p-phenoxy phenyl, o-, m-, p-nitrophenyl, p-nitro-o-cresyl, o-nitro-p-cresyl, o-, m-, p-chlorophenyl, 2,4-dichlorophenyl, 2,4,5-trichlorophenyl, 2,4,6-trichlorophenyl, pentachlorophenyl, the isomeric bromophenyls, 2,4-dibromophenyl, 4,6-dichloro-o-cresyl, p-acetyl phenyl, p-methyl mercaptophenyl, 3-methyl-4-acetyl phenyl, p-methyl mercaptophenyl, 3,5-dimethyl-4-methyl mercaptophenyl, 4-thienyl mercaptophenyl, 3-cyanophenyl, 4-cyanophenyl, 3-(methylcarboxyl)-phenyl, 4-(ethylcarboxyl)-phenyl, 4-(phenylcarboxyl)-phenyl,3-(N-dimethylaminocarboxyl)-phenyl, 4-(N-methylphenylaminocarboxyl)-phenyl, 3-dimethyl aminophenyl, 4-diethyl aminophenyl, 4-(N-methylispropylamino)-phenyl, 4-dimethyl amino-3-methyl phenyl, 4-(phenylmethlamino)-phenyl, 4-methyl sulphonyl phenyl, 4-phenyl sulphonyl phenyl, 2,6-dichloro-4-phenyl sulphonyl phenyl, 4-phenoxy sulphonyl phenyl, 4-di-methyl aminosulphonyl phenyl, 3-(N-methylphenylamino)-sulphonyl phenyl.

If n of formula I represents the number 0 compounds of formula (III) result

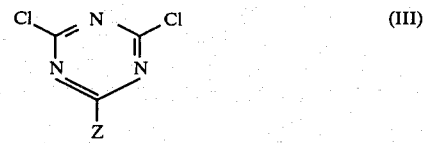
(III)

in which

Z represents hydrogen, alkyl or aryl.

Suitable alkyl radicals are optionally substituted straight-chain and branched chain alkyl radicals with 1 to 10 carbon atoms, preferably with 1 to 6 carbon atoms and more especially with 1 to 3 carbon atoms, for example methyl, ethyl, n-propyl, isopropyl, n-butyl, isobutyl, the isomeric pentyl, hexyl and decyl radicals. Suitable aryl radicals are, for example, phenyl, naphthyl, optionally substituted by a) alkyl radicals with 1 to 4 carbon atoms, for example the isomeric cresyl radicals, b) halogen, for example, the isomeric chlorophenyls or c) alkoxy radicals with 1 to 4 carbon atoms, for example, the isomeric methoxy phenyl radicals.

Reaction of the aromatic dihydroxy or polyhydroxy compounds with 4,6-dichloro-s-triazines may be carried out in the melt at 100° to 250° C, preferably at 150° to 220° C and more especially at 170° to 200° C. The hydrogen chloride formed simultaneously escapes from the melt in gaseous form at these temperatures. It is of course also possible to apply reduced pressure, preferably up to about 0.01 bar and more especially between about 0.2 and about 0.8 bar in order to remove the hydrogen chloride. However, the reaction may also be carried out in solution and/or in suspension in the presence of about 1 mol of base per mol of hydrogen chloride to be eliminated at temperatures in the range from about 0° to about 150° C, preferably at temperatures in the range from 0° to about 100° C and more especially at temperatures in the range from about 20° to 70° C.

Solvents suitable for condensation in solution and/or suspension are, for example, water, lower aliphatic alcohols such as methanol, ethanol, propanol, isopropanol; aliphatic ketones such as acetone, methyl ethyl ketone, diethyl ketone methyl isopropyl ketone, methyl isobutyl ketone; aliphatic or aromatic hydrocarbons, preferred aliphatic hydrocarbons being the fractions accumulating during distillation of the naturally occurring mixtures, such as petroleum ether, light petrol, petrol, whilst benzene, toluene and the xylenes are mentioned as examples of aromatic hydrocarbons: aliphatic and atomatic chlorinated hydrocarbons, such as dichloromethane dichloroethane, perchloroethylene, chlorobenzene, dichlorobenzene; ethers such as diethyl ether, diisopropyl ether; nitro hydrocarbons such as nitromethane, nitrobenzene, nitrotoluene, amides such as dimethyl formamide and dimethyl acetamide.

Bases suitable for condensation in solution and/or suspension are, for example, alkali hydroxides such as sodium hydroxide, potassium hydroxide; alkali carbonates such as sodium carbonate, potassium carbonate; alcoholates such as sodium methylate, potassium-tert-butylate, and also tertiary amines such as triethyl amine, diethyl aniline and pyridine.

In general, reaction of the aromatic dihydroxy or polyhydroxy compounds with 4,6-dichloro-s-triazines is carried out by combining the reactants in the particular quantities selected and heating the resulting reaction mixture to the desired reaction temperature selected. The reaction is complete when the evolution of hydrogen chloride ceases. It is also possible, by measuring the quantity of hydrogen chloride evolved, to determine whether the theoretically calculated quantity has been eliminated, signifying completion of the reaction. In cases where condensation is carried out in the melt, there is generally no need for the condensation product to be further worked up and purified.

Condensation may also be carried out in solution and/or in suspension. To this end, the dihydroxy or polyhydroxy compound is dissolved and/or suspended in the solvent selected and the corresponding quantities of 4,6-dichloro-s-triazines are added to the base. The individual reactants may be added in any order.

The progress and end point of the reaction may be followed and determined, respectively, by known analytical methods from the increase in concentration of chlorine ions. On completion of the reaction, the reaction mixture may be worked up by the usual methods. The hydrochloride of the base used which is formed as secondary product is best initially separated off or dissolved in water and the aqueous solution separated off. The solvent may then be removed, for example by distillation, and the condensation product isolated. The condensation product is hereinafter referred to as the condensate.

Subsequent reaction of the condensate formed with halogen cyanides may be carried out by conventional methods. For example, the condensate and cyanogen halide may be initially introduced in suspension and/or solution in a solvent, followed by addition of the base, optionally in dissolved form. However, the condensate may also be initially introduced, followed by addition of the cyanogen halide and base, both optionally in dissolved form, or the cyanogen halide may be initially introduced and the condensate and base subsequently added, both optionally in dissolved form.

The solvents used may be the solvents employed for the first stage of the process according to the invention. It is also possible to use the solvents normally used for the reaction of phenolic hydroxyl groups with cyanogen halide. The reaction may also be carried out in aqueous suspension and/or in solution, suspension or emulsion using mixtures or emulsions of the above-mentioned solvents with water.

The bases used for this stage of the reaction may be the bases mentioned in reference to the condensation stage and also the bases normally used for the reaction of phenolic hydroxy groups with cyanogen halide.

Cyanogen chloride or cyanogen bromide, both of which are readily commercially obtainable, are particularly suitable for use as the cyanogen halide component. In general, a molar ration of phenolic hydroxy group to cyanogen halide to base of 1 : 1 : 1 is maintained, although a slight excess of cyanogen halide can be advantageous. The reaction may be carried out at temperatures in the range from −40° to +65° C, although it is preferably carried out at temperatures in the range from 0° to 30° C. In cases where cyanogen chloride is used, the reaction is preferably carried out at a temperature below its boiling point (13° C), although in cases where cyanogen bromide is used the reaction may be carried out at the upper end of the above-mentioned temperature range, for example at a temperature above 50° C.

On completion of the reaction the hydrochloric acid salt formed is separated off by a conventional technique, the methods used being governed by the type of solvent employed. In pure organic solution, the chloride formed is generally completely or partly precipitated and may be mechanically separated off by conventional methods. However, it may also be dissolved with water in cases where water-immiscible solvents are used, and separated off in the form of an aqueous solution. In cases where aqueous organic emulsions are used, it may be at least partly dissolved in the aqueous phase and completely dissolved by the addition of more water and separated off with the aqueous phase after breaking of the emulsion. After the solvent has been removed in the usual way, the s-triazine prepolymer is obtained in high yields.

It may also be advantageous to carry out the condensation reaction and subsequent reaction of the condensate formed with halogen cyanide in a so-called one-pot process. In this case, it may be advantageous to carry out condensation in the presence of a solvent, and to use the same solvent and, optionally, the same base for both stages of the process.

Aromatic dihydroxy or polyhydroxy compounds, which may be used as starting materials in the process according to the invention, are known in large numbers. In practice, it is possible to use any aromatic and aromatic-heterocyclic, optionally substituted compounds with two or more phenolic hydroxy groups, providing the substituents, if any, are stable and do not themselves react under the conditions of the process according to the invention.

Preferably the aromatic di- and polyhydroxy compounds correspond to the general formula (IV)

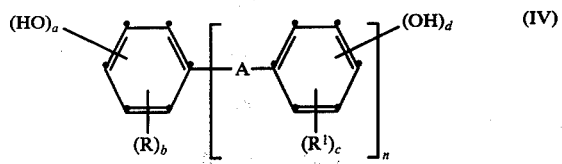

in which
  $a$ is the number 1, 2 or 3,
  $b$ is 5 - $a$,
  $c$ is 5 - $d$,
  $d$ is the number 1, 2 or 3, with the condition that the the sum of a $a$ and $d$ ($a + d$) results in one of the numbers 2 to 4, preferably the numbers 2 or 3, more especially the number 2, if $n = 0$; and in one of the numbers 2 to 6, preferably for 2 to 4, more especially for 2, if $n \geq 1$;
  $n$ is the number 0, 1, 2 and 3 and
  R has the same meaning as given in formula (V) and A and
  R¹ respectively the same meaning as given in formula (VI).

The aromatic hydroxy compounds which may be used in the process according to the invention correspond in particular to the general formula (V)

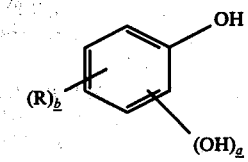

in which
  R represents hydrogen, halogen, alkyl or phenyl, two or more radicals R may be the same or different or two radicals R which substitute adjacent C-atoms may form with those carbon atoms a carbocyclic or heterocyclic 5-membered or 6-membered ring,
  $a$ is the number 1, 2 or 3 and
  $b = 5-a$.
  $a$ is preferably the number 1 or 2, more especially the number 1.

Of the radicals, R, preferably one or two but more especially one has a meaning other than hydrogen, whilst the other represent hydrogen.

Another group of the aromatic dihydroxy and polyhydroxy compounds which may be used in the process according to the invention corresponds in particular to the formula

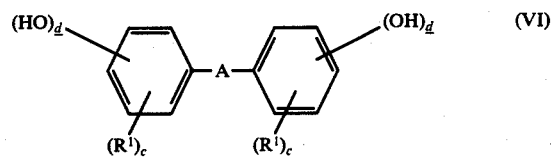

in which
  A represents oxygen, the sulpho group (—SO₂—) the carbonyl group (—CO—), the carbonyldioxy group

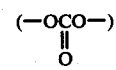

a CH₂-chain with up to 6 and preferably with up to 3 carbon atoms, which may optionally be substituted by lower alkyl radicals, preferably methyl, or phenyl, a cycloaliphatic or aromatic 5-membered or 6-membered ring or a direct bond,
  R¹ has the meaning defined above for R or represents the group

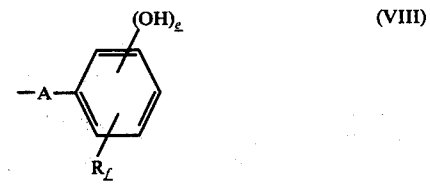

in which
  A and R are defined above,
  $e$ is the number 1, 2 or 3 and
  $f = 5$-$e$,
  $c = 5$-$d$ and
  $d$ is the number 1, 2 or 3.
  $d$ and $e$ are preferably the numbers 1 or 2, more especially the number 1.
  Preferably R¹ stands for R.

Of the $c$ radicals $R^1$ and $f$-radicals R, preferably one or two, but more especially one, radical(s) has a meaning other than hydrogen, whilst the other represent hydrogen.

Of the halogens (fluorine, chlorine, bromine and iodine), fluorine, chlorine and bromine are preferred.

Suitable alkyl radicals are straight-chain and branched chain alkyl radicals with up to 9 carbon atoms and preferably with up to 5 carbon atoms, for example methyl, ethyl, propyl isopropyl, n-butyl, isobutyl, t-butyl and the isomeric pentyl radicals, more especially methyl and ethyl and tert-butyl.

The following compounds are examples of compounds corresponding to the general formulae IV and V: o-, m-, p-dihydroxy benzene, 2-tert-butyl hydroquinone, 2,4-dimethyl resorcinol, 2,5-di-tert-butyl hydroquinone, tetramethyl hydroquinone, 2,4,6-trimethyl resorcinol, 2,6,-di-tert-butyl hydroquinone, 4-chlororesorcinol, 4-tert-butyl pyrocatechol, dihydroxy naphthalenes such as, for example, 1,4-, 1,5-, 1,6-, 1,7-, 2,6-, and 2,7-dihydroxy naphthalene.

The following are examples of compounds corresponding to the general formulae IV and VI: dihydroxy diphenyls such as, for example, 4,4'-dihydroxy diphenyl, 2,2'-dihydroxy diphenyl,
3,3', 5,5'-tetramethyl-4,4'dihydroxy diphenyl,
3,3', 5,5'-tetrachloro-4,4'-dihydroxy diphenyl,
3,3', 5,5'-tetrachloro-2,2'-dihydroxy diphenyl,
2,2', 6,6'-tetrachloro-4,4'-dihydroxy diphenyl,
4,4'-bis-[(3-hydroxy)phenoxy]-diphenyl,
4,4'-bis-[(4-hydroxy)-phenoxy]-diphenyl,
2,2'-dihydroxy-1,1'-binaphthyl; dihydroxy diphenyl ethers, such as for example 4,4'-dihydroxy diphenyl ether,
3,3', 5,5'-tetramethyl-4,4'-dihydroxy diphenyl ether,
3,3', 5,5'-tetrachloro-4,4'-dihydroxy diphenyl ether,
4,4'-bis-[p-hydroxyphenoxy]-diphenyl ether,
4,4'-bis-[p-hydroxyphenylisopropyl]-diphenyl ether,
4,4'-bis-[p-hydroxy-phenoxy]-benzene,
4,4'-bis-[p-hydroxy-phenoxy]-diphenyl ether,
4,4'-bis-[4(4-hydroxyphenoxy)-phenylsulphone]-diphenyl ether,
diphenyl sulphones, such as for example 4,4'-dihydroxy diphenyl sulphone,
3,3', 5,5'-tetramethyl-4,4'-dihydroxy-diphenyl sulphone,
3,3', 5,5'-tetrachloro-4,4'-dihydroxy-diphenyl sulphone,
4,4'-bis-[p-hydroxyphenylisopropyl]-diphenyl sulphone,
4,4'-bis-[(4-hydroxy)-phenoxy]-diphenyl sulphone,
4,4'-bis-[(3-hydroxy)-phenoxy]-diphenyl sulphone,
4,4'-bis-[4-(4-hydroxy phenyl-isopropyl)-phenoxy]-diphenyl sulphone,
4,4'-bis-[4-(4-hydroxyphenyl-sulphone)phenoxy]-diphenyl sulphone,
4,4'-bis-[4-(4-hydroxy)diphenoxy]-diphenyl sulphone, dihydroxy diphenyl alkanes, such as for example
4,4'-dihydroxy-diphenyl methane,
4,4'-bis-[p-hydroxyphenyl]-diphenyl methane,
2,2'-bis-(p-hydroxyphenyl)-propane,
2,2-bis-(3,5-dimethyl-4-hydroxyphenyl)-propane,
2,2-bis-(3,5-dichloro-4-hydroxyphenyl)-propane,
1,1-bis[p-hydroxyphenyl]-cyclohexane,
bis-[2-hydroxy-1-naphthyl]-methane,
1,2-bis-[p-hydroxyphenyl]-1,1, 2,2-tetramethyl ethane,
4,4'dihydroxy benzophenone,
4,4'-bis-(4-hydroxy)phenoxy-benzophenone,
1,4-bis-[p-hydroxyphenylisopropyl]-benzene, phluoroglucinol, pyrogallol, 2,2', 5,5'-tetrahydroxy-diphenyl sulphone.

The process according to the invention is illustrated by the following reaction equations:

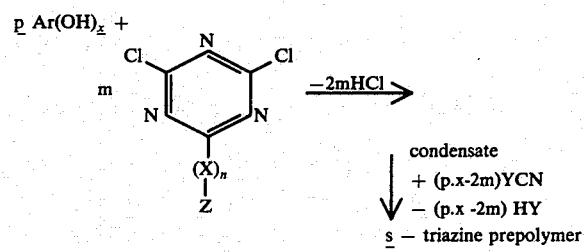

In the above equation, Ar represents an aromatic radical of general formula (IV) or (VI), Y represents halogen, $x$ is a number from 2 to 6, $m$ and $n$ are integers which fulfil the condition $n.x > 2m$.

The number of cyanate groups still present in the s-triazine prepolymer is determind by the ratio of the numbers $n$, $m$ and $x$ which also determines the degree of crosslinking of the s-triazine prepolymer.

The process according to the invention may be illustrated, for example, by the following exemplary equation, in which the formulae for the condensate and the s-triazine prepolymer are shown in idealised form:

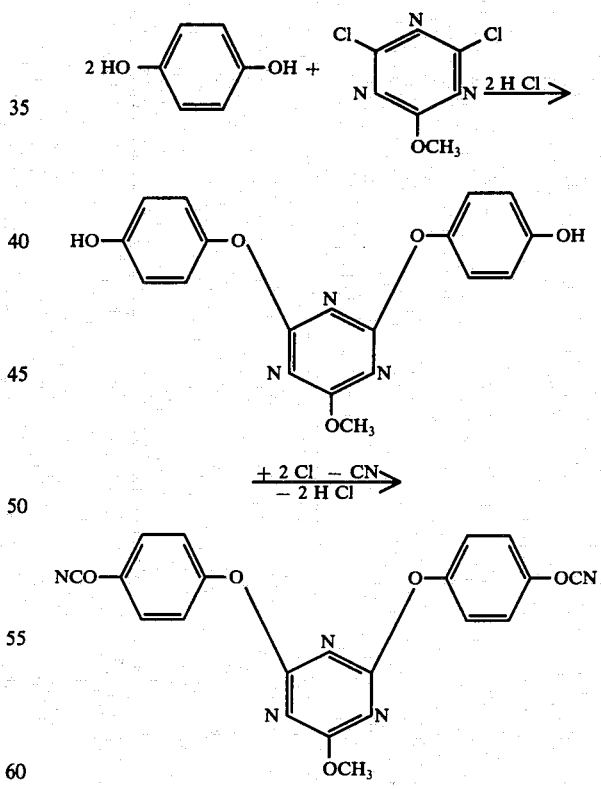

The new s-triazine prepolymers which may be obtained by the process according to the invention are valuable oligomers. They may be polymerised by known processes, for example by the process described in German Auslegeschrift No. 1,190,184 to form valuable high molecular weight polytriazines, which may be used as reinforced plastics, cast resins, moulding materials, adhesives and coating. Polymerisation is carried out, for example, at temperatures in the range from 0° to 200° C, optionally in the presence of a polymerisation activator such as an acid base a salt or a compound of phosphorus.

EXAMPLE 1

18 g (0.1 Mol) of 4,6-dichloro-2-methoxy-s-triazine were dissolved with 45.6 g (0.2 mol) of 2,2-bis-(p-hydroxyphenyl)-propane in 200 ml of isopropanol. 20.2 g (0.2 mole) of triethyl amine, dissolved in 50 ml of isopropanol, were added dropwise to the resulting solution with stirring at 30° to 40° C. The reaction mixture was then boiled under reflex for 6 hours. The triethyl ammonium chloride precipitated was filtered off under suction and washed with 100 ml of isopropanol. The combined isopropanol phases were concentrated, the residue taken up in 200 ml of methylene chloride and extracted with water. The methylene chloride was distilled off, leaving a viscous oil. The reaction product was dissolved with 13.5 g (0.22 mol) of cyanogen chloride in 200 ml of dimethyl acetamide at 0° C. 20.2 g (0.2 mol) of triethyl amine were added dropwise with stirring to the resulting solution at 0° C. On completion of the reaction, the triethyl ammonium chloride precipitated was filtered off under suction, the solvent distilled off and replaced by 200 ml of methylene chloride. The methylene chloride solution was washed with water and the solvent subsequently distilled off. 57 g (93% of the theroetical yield) of cyanate resin with the band characteristic of the cyanate group in the IR spectrum at 4.45$\mu$ were thus obtained.

EXAMPLE 2

20.8 (0.1 mole) of 4,6-dichloro-2-isopropyloxy-s-triazine and 45.6 g (0.2 mol) of 2,2-bis-(p-hydroxyphenyl)-propane were reacted with 20.2 g (0.2 mol) of triethyl amine in 250 ml of acetone in the same way as in Example 1. The reaction mixture was then boiled under reflux for 8 hours. The triethyl ammonium salt precipitated is then filtered off under suction, the solvent distilled off in vacuo and replaced by 200 ml of methylene chloride. The methylene chloride solution was washed twice with 100 ml of water and dried. 13.5 g (0.22 mol) of cyanogen chloride were added to this solution at 0° C. 20.2 g (0.2 mol) of triethyl amine were added to this solution at 0° C. 20.2 g (0.2 mol) of triethyl amine were added dropwise with stirring over a period of 1 hour in such a way that the temperature was kept at 0° C. On completion of the reaction, the triethyl ammonium salt precipitated was filtered off under suction and washed with methylene chloride. The methylene chloride phases were combined and washed with water. Drying and removal of the solvent by distillation leaves 61 g (95% of the theoretical yield) of cyanate resin with an IR-band at 4.5$\mu$.

EXAMPLE 3

22.4 g (0.1 mol) of 4,6-dichloro-2-(2-methoxyethoxy)-s-triazine and 53.6 g (0.2 mol) of 1,1-bis-(p-hydroxyphenyl)-cyclohexane were reacted with 20.2 g (0.2 mol) of triethyl amine in 300 ml of isopropanol in the same way as in Example 1. The reaction mixture was then boiled under reflux for 8 hours. The triethyl ammonium chloride was filtered off under suction and washed with isopropanol. The combined isopropanol phases were concentrated and the residue was taken up in 300 ml of methylene chloride and extracted with water. The solvent was distilled off. The viscous oil obtained was dissolved in 300 ml of dimethyl acetamide, followed by the addition at 0° C of 13.5 g (0.22 mol) of cyanogen chloride. 20.2 g (0.2 mol) of triethyl amine were added dropwise to the resulting solution with stirring at 0° C. On completion of the reaction, the triethyl ammonium chloride was filtered off under suction, the solvent distilled off in vacuo and subsequently replaced by methylene chloride. The methylene chloride solution was washed with water, dried and concentrated, giving 70 g (95% of the theoretical) of cyanate resin with the typical IR-band at 4.5$\mu$.

EXAMPLE 4

24.2 g (0.1 mol) of 4,6-dichloro-2-phenoxy-s-triazine and 22 g (0.2 mol) of resorcinol were condensed with 20.2 g (0.2 mol) of triethyl amine in the same way as in Example 1. The reaction product was then reacted with 13.5 g (0.22 mol) of cyanogen chloride and 20.2 g (0.2 mol) of triethyl amine as in Example 1. 42 g (96% of the theoretical) of cyanate resin with an IR-band at 4.5$\mu$ were obtained.

EXAMPLE 5

41.5 g (0.1 mol) of 4,6-dichloro-2-(pentachlorophenoxy)-s-triazine and 45.6 g (0.2 mol) of 2,2-bis-(p-hydroxyphenyl)-propane were condensed as in Example 1 with 20.2 g (0.2 mol) of triethyl amine. The condensate was subsequently reacted with 13.5 g (0.22 mol) of cyanogen chloride and 20.2 g (0.2 mol) of triethylene amine in 300 ml of dimethyl acetamide. 80 g (94% of the theoretical yield) of cyanate resin (IR-band at 4.5$\mu$) were obtained.

EXAMPLE 6

31.6 g (0.1 mol) of 4,6-dichloro-2-(p-phenyl phenoxy)-s-triazine and 37.2 g (0.2 mol) of 4,4'-dihydroxy diphenyl are condensed as in Example 1. After reaction with 13.5 g (0.22 mol) of cyanogen chloride and 20.2 g (0.2 mol) of triethyl amine, cyanate resin (OCN-band at 4.5$\mu$) was obtained in a yield of 62 g (93% of the theoretical yield).

EXAMPLE 7

45.6 g (0.2 mol) of 2,2-bis-(p-hydroxyphenyl)propane and 22.6 g (0.1 mol) of 4,6-dichloro-2-phenyl-s-triazine were reacted with 20.2 g (0.2 mol) of triethyl amine in 200 ml of acetone at a temperature of 20° C. On completion of the reaction, the reaction mixture was kept for 1 hour at 50° C. The solvent was then distilled off and the residue taken up in 300 ml of water. The condensation product was filtered off under suction, washed with water and dried. Yield: 58 g (95% of the theoretical yield). 61 g (0.1 mol) of the condensate were dissolved in 200 ml of acetone, followed by the addition at 0° C of 13.5 g (0.22 mol) of cyanogen chloride. 20.2 g(0.2 mol) of triethyl amine were then added dropwise with stirring at 0° C. On completion of the reaction, the triethyl amine hydrochloride was filtered off and the acetone distilled off. The residue was taken up in 200 ml of toluene and extracted twice by shaking with 100 ml of water. Removal of the toluene by distillation left 65 g (98% of the theoretical yield) of s-triazine prepolymer. The product obtained was readily characterised by a typical band in the IR-spectrum for the — O — C≡N— group at about 4.5$\mu$.

EXAMPLE 8

22 g (0.2 mol) of hydroquinone and 22.6 g of 4,6-dichloro-2-phenyl-s-triazine were thoroughly mixed and the resulting mixture slowly heated to 220° C. The HCl gas evolved was removed under a vacuum of 0.7 bar. On completion of the reaction, the condensation product was taken up in 200 ml of isopropanol, followed by the addition at 0° C of 13.5 g (0.22 mol) of cyanogen chloride. 20.2 g (0.2 mol) of triethyl amine were added dropwise over a period of 45 minutes at 0° to + 5° C. On completion of the reaction, the solvent was distilled off and replaced by 200 ml of methylene chloride. The methylene chloride phase was extracted twice by shaking with 100 ml of water. Removal of the solvent leaves 40 g (95% of the theoretical yield) of s-triazine prepolymer in the form of a wax-like resin with a characteristic IR-band at 4.5μ.

EXAMPLE 9

22g (0.2 mol) of resorcinol and 22.6 g (0.1 mol) of 4,6-dichloro-2-phenyl-s-triazine were reacted under nitrogen with 80 ml of 10% NaOH in 200 ml of isopropanol. On completion of the reaction, the reaction solution was diluted with 800 ml of water and the condensation product filtered off and dried. Yield: 42 g (94% of the theoretical yield.

20.2 g (0.2 mol) of triethyl amine were added dropwise to 44.6 g (0.1 mol) of condensate and 13.5 g (0.22 mol) of cyanogen chloride in 200 ml of dimethyl acetamide. On completion of the reaction, the hydrochloride precipitated was filtered off under suction and the solvent removed by distillation in vacuo, leaving 40.5 g (96% of the theoretical yield) of resin with the characteristic IR-band at 4.5μ.

EXAMPLE 10

45.6 g (0.2 mol) of 2,2-bis-(p-hydroxyphenyl)-propane and 16.4 g (0.1 mol) of 4,6-dichloro-2-methyl-s-triazine were reacted with 20.2 g (0.2 mol) of triethyl amine in 200 ml of acetone in the same way as described in Example 1. The condensate obtained was reacted with 13.5 g (0.22 mol) of cyanogen chloride and 20.2 g (0.2 mol) of triethyl amine in 200 of dimethyl formamide at 0° C in the same way as described in Example 1. 57 g (95% of the theoretical yield) of resin with an IR-band at 4.5μ were obtained.

EXAMPLE 11

10 g of the s-triazine prepolymer obtained in accordance with Example 1 were heated for 5 hours to 160° C. A high molecular weight polytriazine was otained after cooling the characteristic IR-bands of the triazine ring at 6.4 and 7.25μ.

I claim:

1. A process for producing an s-triazine prepolymer which comprises condensing an aromatic polyhydroxy compound with 0.01 to less than ½ mol of a 4,6-dichloro-s-triazine per hydroxy group of said polyhydroxy compound and subsequently reacting the product of said condensation with a halogen cyanide in the presence of a base, the molar ratio of hydroxy groups to cyanogen halide to base being about 1:1:1, said condensation being carried out in the melt at a temperature of 100° to 250° C. or in solution or suspension in the presence of about 1 mol of base per mol of hydrogen chloride to be eliminated at a temperature of from about 0° to 150° C., said reaction of said condensation product with cyanogen halide in the presence of a base being carried out at a temperature of from −40° to 65° C., each of said bases being selected from the group consisting of tertiary amines, alkali metal hydroxides, alkali metal carbonates and alkali metal alcoholates, said polyhydroxy compound being of the formula

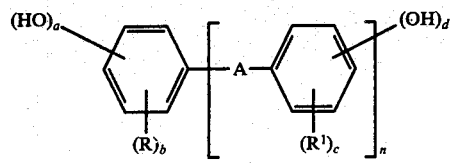

wherein $a$ is 1, 2 or 3, $b$ is 5 - $a$; $c$ is 5 - $d$; $d$ is 1, 2 or 3 with the proviso that $a + d$ is from 2 to 4 if $n$ is 0 and is 2 to 6 if $n$ is 1; $n$ is 0, 1, 2 or 3; R is hydrogen, halogen, alkyl or phenyl; A is —O—, —SO$_2$—, —CO—,

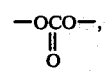

a CH$_2$ chain having up to 6 carbon atoms, a CH$_2$ chain having up to 6 carbon atoms substituted by lower alkyl, a CH$_2$ chain having up to 6 carbon atoms substituted by phenyl, a divalent cycloaliphatic or aromatic 5- or 6-membered ring or a single bond and R$^1$ is the same as R or

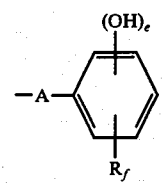

wherein A and R are as defined above, $e$ is 1, 2 or 3 and $f$ is 5-$e$ and said 4,6-dichloro-s-triazine is of the formula

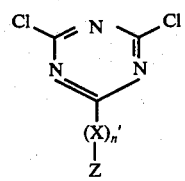

wherein $n'$ is 0 or 1; Z is hydrogen, alkyl or aryl; X is —O—, —S—, —NH— or —NZ'— and Z and Z' are alkyl, cycloalkyl or aryl.

2. The process of claim 1 wherein said condensation is carried out in the melt at a temperature of 150° to 200° C.

3. The process of claim 1 wherein said condensation is carried out in solution or suspension at a temperature of from 0° to about 100° C.

4. The process of claim 1 wherein the product of said condensation is reacted with said cyanogen halide at a temperature of from 0° to 30° C.

5. An s-triazine prepolymer prepared by the process of claim 1.

* * * * *